US00PP34233P2

(12) United States Plant Patent
Bedard

(10) Patent No.: US PP34,233 P2
(45) Date of Patent: May 17, 2022

(54) ***FLORIBUNDA* ROSE PLANT NAMED 'WEKCRYPEPLOS'**

(50) Latin Name: *Rosa hybrida*
Varietal Denomination: WEKcrypeplos

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/300,838

(22) Filed: Nov. 22, 2021

(51) Int. Cl.
*A01H 6/74* (2018.01)
*A01H 5/02* (2018.01)

(52) U.S. Cl.
USPC ..... Plt./141

(58) Field of Classification Search
USPC ..... Plt./141
See application file for complete search history.

(56) References Cited

U.S. PATENT DOCUMENTS

PP23,555 P2 4/2013 Kordes
PP24,743 P3 8/2014 Carruth

OTHER PUBLICATIONS

Rose (Rosa 'Dr. Huey') in the Roses Database, Garden.org., https://garden.org/plants/view/1545/Rose-Rosa-Dr-Huey/, 9 pages, last visited Dec. 15, 2021.
Prior Product Sales, 8 pages, Dec. 7, 2020.
Weeks Roses Wholesale Rose Catalog, "Silver Lining", 27 pages, 2021.

*Primary Examiner* — Annette H Para
(74) *Attorney, Agent, or Firm* — McKee, Voorhees & Sease, PLC

(57) ABSTRACT

A new variety of *Floribunda* rose suitable for garden decoration, having flowers of silver lavender coloration.

1 Drawing Sheet

Classification The present invention relates to a new *Rosa hybrida* plant.

Variety denomination The new plant has the varietal denomination 'WEKcrypeplos'.

BACKGROUND OF THE INVENTION

This invention relates to a new and distinct variety of *Floribunda* Rose. It has a non-disseminated seedling of my creation as its seed parent with the following genetic origin Crystalline x Perfume Perfection and as its pollen parent the variety known as 'WEKstameda' (U.S. Plant Pat. No. 24,743).

SUMMARY OF THE INVENTION

Among the features which distinguish the new variety from other presently available and commercial rose cultivars known to the inventor are the following combinations of characteristics: its unique silver lavender flower coloration, its abundant blooms and its excellent color stability throughout the life of the flower. The plant has an upright bushy moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKcrypeplos' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKcrypeplos' bears medium to large sized flowers (about 8.5 to about 12.3 cm. in diameter) of silver lavender coloration, the non-disseminated seedling bears significantly smaller flowers (about 6.9 to about 8.2 cm. in diameter) of lavender blue coloration. The new variety has a slight tea to somewhat fruity with hints of spices fragrance, whereas the seed parent has a strong fruity fragrance.

The new variety may be distinguished from its pollen parent, 'WEKstameda' by the following combination of characteristics: whereas 'WEKcrypeplos' bears medium to large sized flowers (about 8.5 to about 12.3 cm. in diameter) of silver lavender coloration, 'WEKstameda' bears smaller flowers (about 8.3 to about 9.1 cm. in diameter) of clear lavender coloration. The new variety has an upright bushy moderately spreading growing habit (about 122 to about 158 cm. spread at the widest point), whereas the pollen parent has a bushy rounded significantly narrower growing habit (about 70 to about 90 cm. spread at the widest point).

COMPARISON WITH THE CLOSEST COMMERCIALLY AVAILABLE CULTIVAR

The new variety may be distinguished from its closest commercially available cultivar, 'KORfriedhar' (U.S. Plant Pat. No. 23,555) by the following combination of characteristics: whereas 'WEKcrypeplos' bears medium to large sized flowers (about 8.5 to about 12.3 cm. in diameter) of silver lavender coloration, 'KORfriedhar' bears significantly smaller flowers (about 6.0 to about 8.0 cm. in diameter) of lavender coloration. The new variety bears very double flowers (about 32 to 52 petals), whereas the closest commercially available cultivar bears very double flowers with significantly heavier petalage (about 70 to 75 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Rancho Cucamonga, Calif. in the month of November. Phenotypic expression may vary with environmental, cultural and climatic conditions, as well as differences in conditions of light and soil.

FLOWER

The new variety sometimes bears its flowers singly, usually in clusters of two to five per stem. Flowers may be borne in regular rounded clusters on strong medium to long stems (about 21 to about 82 cm.). The cluster ranges from about 13.0 to about 23.0 cm. in diameter. Outdoors, the plant blooms abundantly and nearly continuously during the growing season. The flowers have a slight tea to somewhat fruity with hints of spices fragrance.

BUD

The peduncle is about 2.2 to about 7.8 cm. in length, of average to somewhat heavy caliper (about 0.2 to about 0.4 cm. in diameter), and usually erect to somewhat stiff. It is moderately rough, with many stipitate glands, and some hairs. Peduncle color is between 146C and 146B sometimes lightly suffused, especially on the side exposed to the sun, with between 187C and 187D.

Before the calyx breaks, the bud is about 1.1 to about 2.0 cm. in diameter at the widest point, about 1.5 to about 2.5 cm. in length, and moderately ovoid to somewhat pointed in shape. The surface of the bud bears between 4 to 6 foliaceous appendages with few stipitate glands and some hairs, usually with slender entire foliaceous parts extending beyond the tip of the bud about ¾ or more of its length. Bud color is between 137C and 137B sometimes lightly suffused, especially on the side exposed to the sun, with between 187B and 187C.

The sepals are 5 per flower, about 2.6 to about 5.1 cm. in length and about 0.6 to about 1.0 cm. in width at the widest point. The outer surface color of the sepal is between 137C and 137B sometimes lightly suffused, especially on the side exposed to the sun, with between 187B and 187C. The outer surface of the sepal is somewhat rough and bears between 0 to 2 foliaceous appendages with few stipitate glands, and some hairs. The inner surface color of the sepal is near 146D broadly bordered by near 137C. After the sepals open, the inner surface color is sometimes lightly suffused, especially on the area exposed to the sun, with between 187A and 187B. The inner surface of the sepal is covered with fine wooly tomentum; sepal margins are entire and lined with few stipitate glands and some hairs. The sepals are moderately permanent, and usually straight in shape with acute apices.

The receptacle of the flower is of medium length (about 0.7 to about 1.0 cm.) and average to somewhat heavy in caliper (about 0.6 to about 1.2 cm. in diameter). The receptacle is cup-shaped in form. Its surface is smooth with some hairs and with moderately thick fleshy walls. The receptacle color is between 144A and 138A.

As the petals open (after the calyx breaks), the bud is about 1.8 to about 2.3 cm. in diameter at the widest point, about 2.3 to about 3.2 cm. in length, and moderately ovoid to somewhat pointed in form. The color of the under surfaces of the newly opened petals is between 27A and 75D sometimes moderately suffused with between 53A and 60A. At the point where the petal attaches, there is a large zone of between 4C and 3D. The color of the upper surfaces of the newly opened petals is between 36B and 76C. At the point where the petal attaches, there is a large zone of between 4C and 3D.

BLOOM

When fully open, the bloom ranges from about 8.5 to about 12.3 cm. in diameter. Petalage is very double with about 32 to 52 petals and about 1 to 9 petaloids irregularly arranged. When partially open, the bloom form is moderately high centered to cupped, and the petals are tightly spiraled to cupped with petal edges moderately reflexed outward. When fully open, the bloom form is more cupped, and the petals are loosely cupped to somewhat undulated with petal edges moderately reflexed outward.

PETALS

The substance of the petals is somewhat heavy and of moderately thin to medium thickness, with upper surfaces moderately shiny to slightly satiny and under surfaces slightly shiny. The petals are about 3.7 to about 6.2 cm. in length and about 2.5 to about 5.9 cm. in width at the widest point. Petal margins are entire.

The outer petals are moderately obovate to somewhat rounded in shape with rounded apices.

The inner petals are broadly obovate in shape with rounded to sometimes somewhat mucronate apices.

Petaloids are about 1.2 to about 3.9 cm. in length and about 0.7 to about 2.5 cm. in width at the widest point. Petaloids are irregularly shaped moderately obovate to somewhat oblanceolate to subulate with rounded apices.

NEWLY OPENED FLOWER

The under surface color of the outer petals is between 69D and lighter than 75D. At the point where the petal attaches, there is a moderately large zone of between 155C and 155B. The upper surface color of the outer petals is between 69D and lighter than 75D. At the point where the petal attaches, there is a large zone of between 155C and 155B.

The under surface color of the intermediate and inner petals is between 69D and 75D. The upper surface color of the intermediate and inner petals is between 69C and 75D.

The under and upper surface colors of the petaloids are similar in coloration to the upper and under surfaces of the intermediate and inner petals.

The general tonality of the newly opened flower is between 69C and 75D.

THREE-DAY-OLD FLOWER

The under surface color of the outer petals is between lighter than 69D and lighter than 75D. At the point where the petal attaches, there is a moderately large zone of between 155C and 155B. The upper surface color of the outer petals is between 69D and lighter than 75D. At the point where the petal attaches, there is a large zone of between 155C and 155B.

The under surface color of the intermediate and inner petals is between 69D and 75D. The upper surface color of the intermediate and inner petals is between 69C and 75D.

The under and upper surface colors of the petaloids are similar in coloration to the upper and under surfaces of the intermediate and inner petals.

The general tonality of the three-day-old flower is between 69C and 75D.

On the spent bloom, the petals usually drop off cleanly.

In November in Rancho Cucamonga, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 160) and are arranged regularly about the pistils; a few are mixed with petaloids. The filaments are of somewhat short to medium length (about 0.4 to about 1.2 cm.) most with anthers. Filaments are between 11A and 8A in color sometimes lightly suffused with near 53D. The anthers are moderately large for the class and all open approximately at the same time. Anther color when immature is near 20A on the external part and near 4D on the internal part. Anther color at maturity is near 163B on the external part and near 200D on the internal part. Pollen is somewhat sparse and between 18C and 19C in color.

FEMALE REPRODUCTIVE ORGANS

Pistils vary in number (average about 135). The styles are moderately uneven, somewhat short to average in length (about 0.4 to about 0.8 cm.), thin in caliper, and loosely bunched to somewhat separated. Stigma color is between 18B and 19B. Style color is between 11D and 155A usually heavily suffused with between 60A and 60B. Ovaries are usually all enclosed in the calyx. The ovaries are of medium size and between 158A and 159C in color.

Hips have not been observed on this variety when grown in Rancho Cucamonga, Calif.

FOLIAGE

The compound leaves are usually comprised of three to seven leaflets and are borne abundantly. The seven-leaflet leaves are about 9.3 to about 16.8 cm. in length and about 7.6 to about 12.8 cm. in width at the widest point, moderately leathery to somewhat crisp in texture on both sides, and glossy in finish on the upper side and matte in finish on the under side. The leaves have a pinnate venation pattern. The terminal leaflets are about 4.1 to about 7.2 cm. in length and about 2.1 to about 4.7 cm. in width at the widest point, shaped moderately ovate to somewhat oval with acute to somewhat acuminate apices and rounded to somewhat acute bases. Their margins are usually simply serrate.

The upper surface color of the mature leaf is between 137A and 137B. The under surface color of the mature leaf is between 147B and 138B. The under and upper colors of the leaf veins on the mature leaf are similar in coloration to the upper and under surfaces colors of the mature leaf. The upper surface color of the young leaf is between 146B and 146C, often heavily suffused with between 187A and 187B. The under surface color of the young leaf is between 147B and 138B, often heavily suffused with between 187B and 187A. The under and upper colors of the leaf veins on the young leaf are similar in coloration to the upper and under surfaces colors of the young leaf.

The rachis is about 4.7 to about 8.2 cm. in length, about 0.1 to about 0.15 cm in width at the widest point, and rough. The upper side is deeply grooved with few hairs and some stipitate glands on the edges of the grooves. The under side of the rachis is rough with few stipitate glands and few small prickles. The rachis color is near 145C on the under side and near 137C on the upper side, often heavily suffused on the young leaves with between 187A and 187B.

The stipules are about 1.7 to about 2.3 cm. in length and medium to somewhat wide in width (about 0.5 to about 0.8 cm.) with moderately short to medium length straight points that usually turn out at an angle of more than 45 degrees and sometimes recurve toward the stem. The under and upper surface color of the stipule is between 137A and 137B often moderately suffused on the new leaves with between 187A and 187B. The upper and under surfaces of the stipules are smooth in texture.

The petiole is somewhat light to average in caliper and rough. The upper side is deeply grooved with few hairs and some stipitate glands on the edges of the grooves. The under side of the petiole is rough with few stipitate glands and few small prickles. The petiole is about 0.2 to about 1.9 cm. in length and about 0.1 to about 0.15 cm in width at the widest point. The petiole color is near 145C on the under side and near 137C on the upper side, often heavily suffused on the young leaves with between 187A and 187B.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Rancho Cucamonga, Calif. The plant's winter hardiness and drought/heat tolerance are yet to be determined.

GROWTH

The plant has an upright bushy moderately spreading medium height growing habit (about 96 to about 140 cm. in height and about 122 to about 158 cm. spread at the widest point), with full branching. It displays vigorous growth and the canes are of somewhat small to medium sized caliper for the class (about 1.2 to about 1.8 cm. in diameter at the widest point).

The color of the major stems is between 137C and 146B. The major stems are rough in texture and they bear some large prickles that are about 0.7 to about 1.4 cm. in length. The large prickles are almost straight to angled slightly downward with a medium length moderately broad oval base; prickle color is between 165A and 200C. The major stem bears few small prickles of similar shape and coloration.

The color of the branches is between 146B and 137B. The branches are rough in texture and they bear some large prickles which are of similar shape to the large prickles on the major stems. The prickles are about 0.5 to about 0.9 cm. in length. Prickle color is between 152C and 152D usually heavily suffused with between 187C and 187D. The branches bear few small prickles of similar shape and coloration.

The color of the new shoots is between 146B and 137B often heavily suffused with between 183A and 187B. The new shoots are rough in texture and they bear some large prickles which are of similar size and shape to the large prickles on the branches; prickle color is between 146C and 152B usually heavily suffused with between 187C and 187B. The shoots bear some small prickles of similar shape and coloration.

I claim:

1. A new and distinct *Floribunda* rose plant of the variety substantially as described and illustrated herein.

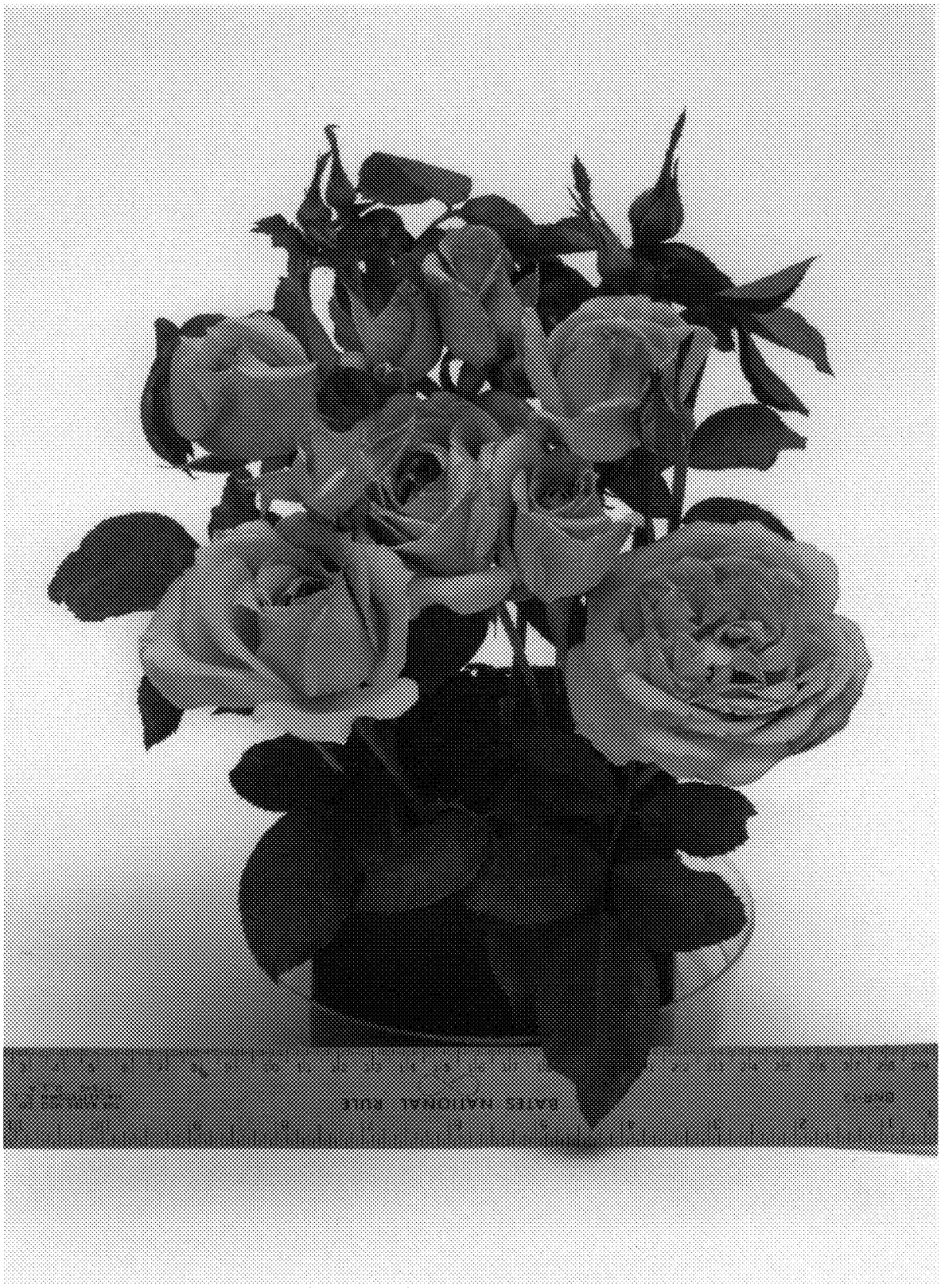

* * * * *